US012201450B2

(12) United States Patent
Curran et al.

(10) Patent No.: US 12,201,450 B2
(45) Date of Patent: Jan. 21, 2025

(54) INTEGRATED MONITORING SYSTEM

(71) Applicant: Fred Bergman Healthcare Pty Ltd, North Sydney (AU)

(72) Inventors: Peter Curran, North Sydney (AU); Michael Spooner, North Sydney (AU)

(73) Assignee: Fred Bergman Healthcare Pty Ltd, North Sydney (AU)

(*) Notice: Subject to any disclaimer, the term of this patent is extended or adjusted under 35 U.S.C. 154(b) by 45 days.

(21) Appl. No.: 18/027,410

(22) PCT Filed: Sep. 20, 2021

(86) PCT No.: PCT/AU2021/051095
§ 371 (c)(1),
(2) Date: Mar. 21, 2023

(87) PCT Pub. No.: WO2022/056607
PCT Pub. Date: Mar. 24, 2022

(65) Prior Publication Data
US 2023/0329638 A1 Oct. 19, 2023

(30) Foreign Application Priority Data
Sep. 21, 2020 (AU) ................................. 2020903382

(51) Int. Cl.
*A61B 5/00* (2006.01)
*A61B 5/08* (2006.01)
(Continued)

(52) U.S. Cl.
CPC .......... *A61B 5/6808* (2013.01); *A61B 5/0816* (2013.01); *A61B 5/14552* (2013.01);
(Continued)

(58) Field of Classification Search
CPC . A61B 5/6808; A61B 5/0816; A61B 5/14552; A61B 5/72; A61B 2562/0219; A61F 13/42; A61F 2013/424
See application file for complete search history.

(56) References Cited

U.S. PATENT DOCUMENTS 6,450,957 B1 * 9/2002 Yoshimi ............... A61B 5/6892
600/595
7,690,378 B1 * 4/2010 Turcott ................ A61B 5/4818
600/501

(Continued)

FOREIGN PATENT DOCUMENTS

| EP | 3 099 224 B1 | 5/2020 |
|---|---|---|
| WO | WO-2015/172246 A1 | 11/2015 |
| WO | WO-2017/131276 A1 | 8/2017 |

OTHER PUBLICATIONS

International Search Report from corresponding International Patent Application No. PCT/AU2021/051095, dated Nov. 19, 2021.
(Continued)

*Primary Examiner* — Nay Tun
(74) *Attorney, Agent, or Firm* — Kusner & Jaffe

(57) ABSTRACT

The present invention relates to a combination of sensors, a system and a method for monitoring incontinence and physiological parameters. The system includes a plurality of electrodes on an absorbent article including an absorbent core to be worn by a wearer being monitored, a device for electrical connection with the electrodes and for monitoring one or more electrical properties of the electrodes indicative of the occurrence of an incontinence event, an oxygen saturation sensor for monitoring the oxygen saturation of the blood of the wearer, and wherein the operation of the oxygen saturation sensor is controlled according to the body position of the wearer.

20 Claims, 11 Drawing Sheets

(51) Int. Cl.
 A61B 5/1455 (2006.01)
 A61F 13/42 (2006.01)
(52) U.S. Cl.
 CPC ............... A61B 5/72 (2013.01); A61F 13/42 (2013.01); *A61B 2562/0219* (2013.01); *A61F 2013/424* (2013.01)

(56) References Cited

U.S. PATENT DOCUMENTS

| | | |
|---|---|---|
| 2008/0058740 A1 | 3/2008 | Sullivan et al. |
| 2013/0096404 A1* | 4/2013 | Colman ............... A61B 5/4818 600/324 |
| 2014/0121473 A1 | 5/2014 | Banet et al. |
| 2019/0374122 A1 | 12/2019 | Kuenzi et al. |

OTHER PUBLICATIONS

Written Opinion from corresponding International Patent Application No. PCT/AU2021/051095, dated Nov. 19, 2021.

* cited by examiner $f(t) = a\Delta BT + b\Delta HR + C\Delta RR + d\Delta RD$
$+ e\Delta \frac{\text{Activity}}{\text{Positive}} + f\Delta \frac{\text{Activity}}{\text{Positive}} + g\Delta SpO_2$ if $f(t)$ > Threshold => Check for disease/infection.

[$SpO_2$, $\Delta BT$, $\Delta HR$, $\Delta RR$, $\Delta RD$, $\Delta Posture$, $\Delta Waste$]

INTEGRATED MONITORING SYSTEM

TECHNICAL FIELD

The present invention relates to a combination of sensors, a system and a method for monitoring incontinence and physiological parameters. The present invention is particularly, although not exclusively, adapted for detecting incontinence events occurring in an incontinence garment and for detecting other parameters that may be indicative of changing health conditions such as respiratory distress or fever.

BACKGROUND OF INVENTION

Incontinence is a condition in which there is an uncontrolled release of discharges or evacuations from the bowel or bladder of an individual. Urinary incontinence refers to loss of bladder control resulting in involuntary or uncontrolled urination. Other forms of incontinence include faecal or bowel incontinence.

Incontinence indicators and detection systems exist but, in most instances, they merely alert a carer to the situation where an incontinence event has occurred and the wearer requires a diaper or pad change. More sophisticated systems exist that are capable of estimating a volume of a bodily output received in an absorbent article worn by a wearer.

Examples of methods and devices for monitoring incontinence are disclosed in Applicant's own WO2007/128038 entitled "Moisture Monitoring System", WO2011/054045 entitled "Improvements in Incontinence Monitoring and Assessment", WO2011/156862 entitled "Apparatus and Method for Analysing Events from Sensor Data by Optimization", WO 2013/003905 entitled "Improvements Relating to Event Detection Algorithms" and WO2019090387 entitled "A System for Managing Incontinence" the entire contents of each of which are hereby incorporated herein by reference.

Such systems can include sensors that are adapted for electrical connection to an electronic device, such as a transceiver, which sends a signal to a processing device when an incontinence event is occurring or has occurred in the absorbent article. The system is configured to measure an electrical variable, such as resistance, of a wetness sensor in the absorbent article and to determine whether an incontinence event has occurred and other characteristics of incontinence events which are occurring or have occurred. Such systems may be adapted to alert a carer to the occurrence of an incontinence event so that the carer may check the article and, if necessary, change the article.

Incontinence indicators and detection systems are characterised by high costs. The high cost of consumables means that existing detection systems are typically only used in aged care facilities during an assessment phase. This is where a new wearer in an aged care facility has their incontinence assessed during a relatively short period, such as about 72 hours. Recently, incontinence indicators and detection systems have been developed that are for use as full-time incontinence indicators or alert systems.

In addition to the cost of devices and consumables, another major challenge in the development of full-time incontinence indicators and detection systems is power management. Full-time incontinence indicators and detection systems ideally involve an electronic device worn by a wearer that includes electronics capable of monitoring the electrical behaviour of a wetness sensor in the absorbent article and a transmitter for wirelessly transmitting data and a battery for powering the device. Preferably, the power consumption of such devices is as low as possible to maximise the life of the battery or, in the case of a rechargeable battery, to maximise the time between charges.

Applicant's own wearable devices for full-time incontinence monitoring and assessment also include an accelerometer to enhance the accuracy and reliability of the incontinence data and associated alerts. The accelerometer provides data useful for determining body position which can be used for the purpose of adjusting urinary volume estimates due to the combined effects of fluid dynamics, positional pressure, and gravity. Determining body position can also be useful for monitoring movement of the wearer and for detecting falls.

Respiratory distress or fever are symptoms that can be life threatening for the elderly and disabled or for babies and infants. In addition to incontinence, it can be desirable to monitor other physiological parameters of elderly or disabled adults and babies or infants. In particular, it can be useful to monitor other parameters that may be indicative of changing health conditions such as respiratory distress or fever.

However, monitoring physiological parameters either alone or in conjunction with monitoring incontinence is challenging to do reliably and effectively. Also, providing a wearable device for full-time incontinence monitoring and assessment as well as for monitoring physiological parameters can increase power consumption requirements to an unacceptable level.

Accordingly, a reliable and cost effective means for full-time detection of incontinence events in an absorbent article worn by a wearer and for full-time monitoring of physiological parameters that may be indicative of changing health conditions such as respiratory distress or fever is desirable.

It is desirable for a wearable device for full-time detection of incontinence events and for monitoring of physiological parameters to have a lowest possible power consumption.

It is desirable for a wearable device for full-time detection of incontinence events and for monitoring of physiological parameters to provide information about incontinence and physiological parameters to a carer within an acceptable time so that appropriate action can be taken.

The discussion of the background to the invention included herein including reference to documents, acts, materials, devices, articles and the like is included to explain the context of the present invention. This is not to be taken as an admission or a suggestion that any of the material referred to was published, known or part of the common general knowledge in Australia or in any other country as at the priority date of any of the claims.

SUMMARY OF INVENTION

Accordingly, in one aspect, the present invention a system for monitoring incontinence and physiological parameters, the system including:
- a plurality of electrodes on an absorbent article including an absorbent core to be worn by a wearer being monitored;
- a device for electrical connection with the electrodes and for monitoring one or more electrical properties of the electrodes;
- an oxygen saturation sensor for monitoring the oxygen saturation of the blood of the wearer;
- wherein the operation of the oxygen saturation sensor is controlled according to the body position of the wearer.

Preferably, a device is operable for monitoring one or more electrical properties of the electrodes indicative of the occurrence of an incontinence event or the status of the absorbent article.

Preferably, the device is configured to receive and process data indicative of the electrical behaviour of the electrodes and determine what information is relevant to determine the status of the absorbent article, for example any one or more of the occurrence of a urinary and/or faecal incontinence event, cumulative volume of wetness present in the absorbent article from multiple incontinence events, the times when incontinence events occur, and the volume of each individual incontinence event.

Preferably, the oxygen saturation sensor comprises a pair of light emitting diodes (LEDs) and a photodetector and a processor for determining oxygen saturation in the blood of the wearer, wherein controlling the operation of the oxygen saturation sensor includes controlling an intensity of light emitted by the LEDs.

Preferably, controlling an intensity of light emitted by the LEDs includes adjusting the intensity of light emitted by the LEDs between different intensity settings.

Preferably, the system includes a processor, preferably on-board the device, adapted to adjust the current provided to the LEDs according to data indicative of the body position of the wearer.

Preferably, the system is configured to adjust the current to cause the LEDs to emit a relatively low intensity of light and to adjust the current adaptively to cause the LEDs to emit a higher intensity of light until reliable sensing is achieved.

Preferably, the processor is adapted to adjust a sensitivity to signals received from the photodetector in addition to or instead of adjusting the current provided to the LEDs.

Preferably, the processor determines the heart rate of the wearer from the signals received from the oxygen saturation sensor.

Preferably, the processor determines the respiration rate and/or the respiration depth of the wearer from the signals received from the oxygen saturation sensor.

Preferably, the processor includes any one or more of a processor in the device, a processor located in a device or server located remotely of the device or a cloud computing processor or processing is distributed among any combination thereof.

Preferably, the body positions include any one or more of a prone position, a seated position and a standing position.

Preferably, the device further includes a body position sensor for detecting the body position of the wearer.

Preferably, the body position sensor includes an inertial measurement unit sensors, preferably an accelerometer, and a processor for processing signals from the inertial measurement unit sensor to determine data indicative of the body position of the wearer.

Preferably, data from the accelerometer is processed to determine movement of the wearer indicative of respiration rate and/or depth of the wearer.

Preferably, the device further includes a contactless temperature sensor for detecting the temperature of the skin of the wearer.

Preferably, the contactless temperature sensor includes an infra-red pyrometer and a processor for processing signals from the pyrometer to determine data indicative of the body temperature of the wearer.

Preferably, the electrodes are comprised of at least two mutually separated flexible conductive electrodes wherein an electrical property of the electrodes being monitored is capacitance.

Preferably, the electrodes are disposed on an outer surface of a water impermeable layer of the absorbent article facing away from the wearer with the absorbent core located on an opposite side of the water impermeable layer facing towards the wearer.

In embodiments, the water impermeable layer comprises at least in part the outer layer of the absorbent article. In embodiments, the water impermeable layer comprises a printed layer or a locally applied layer or a strip provided on the outer layer of the absorbent article, which outer layer may itself be water permeable or impermeable, wherein the electrodes are disposed longitudinally on the water impermeable layer with the water impermeable layer extending a distance laterally from the electrodes. The distance that the water impermeable layer extends laterally from the electrode may be any one of 1 mm to 15 mm or any increment therebetween.

Preferably, for absorbent articles containing an extruded outer layer, wherein a plasticised film is extruded onto a non-woven fabric, the electrodes are disposed on the non-woven fabric prior to extrusion of the plasticised film thereon. In embodiments, the non-woven fabric is locally prepared or conditioned, such as with a printed varnish layer, prior to application of the electrodes.

Preferably, the system includes a processor, which may be the same processor described above, for monitoring the capacitance of the electrodes to determine data indicative of the occurrence of an incontinence event in the absorbent article.

In another aspect, the invention provides a method for monitoring incontinence and physiological parameters, the method including:
  electrically connecting a device to electrodes applied to an absorbent article worn by a wearer;
  monitoring an electrical property exhibited by the electrodes;
  detecting a change in the electrical property due to the presence of fluid from a urinary incontinence event or constituents of a faecal incontinence event in the absorbent pad;
  determining from the change in the electrical property the occurrence of a urinary or faecal incontinence event;
  receiving and processing data from an oxygen saturation sensor for monitoring oxygen saturation in the blood of the wearer;
  receiving and processing data from a body position sensor for determining the body position of the wearer; and
  controlling the operation of the oxygen saturation sensor according to the determined body position of the wearer.

Preferably, controlling the operation of the oxygen saturation sensor includes controlling an intensity of light emitted by a pair of light emitting diodes (LEDs) and/or controlling adjusting a sensitivity to signals received from a photodetector.

Preferably, the method includes determining the heart rate of the wearer from the signals received from the oxygen saturation sensor.

Preferably, the method includes determining the respiration rate and/or the respiration depth of the wearer from the signals received from the oxygen saturation sensor.

Preferably, receiving and processing data from a body position sensor includes receiving signals from an accelerometer.

Preferably, data from the accelerometer is processed to determine movement of the wearer indicative of respiration rate and/or depth.

In another aspect, the invention provides a system for monitoring physiological parameters, the system including:

a wearable device including light emitting diodes (LEDs), a photodetector and a processor, wherein the LEDs emit two wavelengths of light to the wearer's body and in response to detecting light reflected from the wearer's body the photodetector exhibits an electrical property;

wherein the processor determines from the electrical property exhibited by the photodetector the respiration rate and/or respiration depth of the wearer.

Preferably, the processor determines from the electrical property exhibited by the photodetector the oxygen saturation of the blood of the wearer.

Preferably, the device includes an accelerometer and data from the accelerometer is processed to determine movement of the wearer that is also indicative of respiration rate and/or depth.

These and other aspects and embodiments of the invention will become apparent from the foregoing summary of the drawings and the detailed description.

BRIEF DESCRIPTION OF DRAWINGS

The present invention will now be described in more detail with reference to embodiments of the invention illustrated in the figures, wherein.

DETAILED DESCRIPTION

Figure 1:
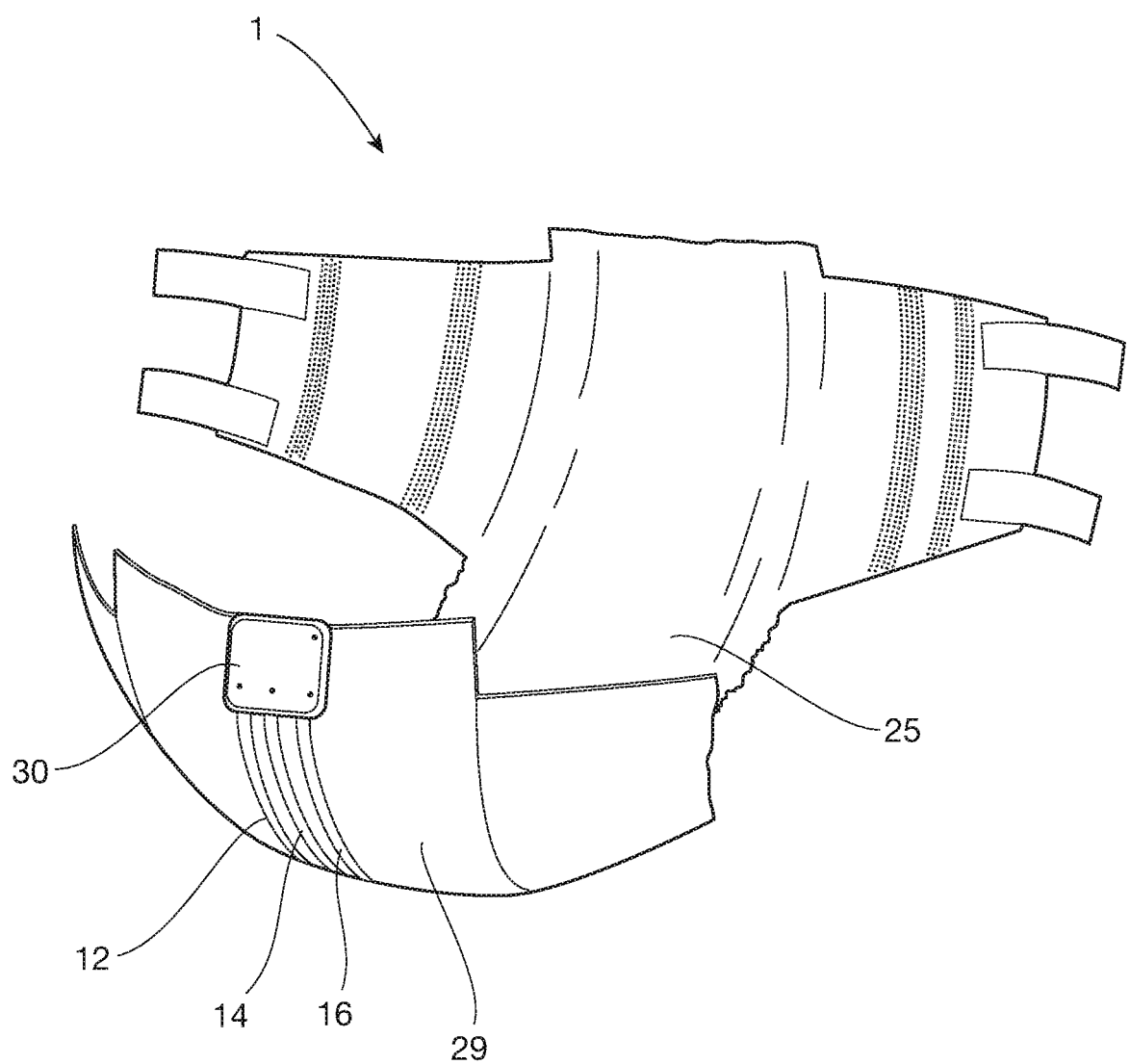
FIG. 1 illustrates a diagrammatic representation of a system in accordance with an embodiment of the invention for monitoring incontinence and physiological parameters including a plurality of electrodes on an absorbent article and a device for electrical connection with the electrodes and including a pulse oximeter, an accelerometer and a temperature sensor.

In one aspect, and with reference to the Figures, the invention relates to a system 1 for monitoring incontinence and physiological parameters. Referring to FIG. 1, the system 1 includes, in part, a plurality of electrodes 12, 14, 16 on an absorbent article 25 including an absorbent core 27, a device 30 for electrical connection with the electrodes 12, 14, 16 and for monitoring an electrical property of the electrodes 12, 14, 16. As described below, the electrodes 12, 14, 16 are adapted for detection of wetness associated with a urinary incontinence event. Optionally a second set of electrodes (not shown) are provided for electrical connection with the device 30. The second set of electrodes are adapted for detection of a faecal incontinence event.

Figure 2:
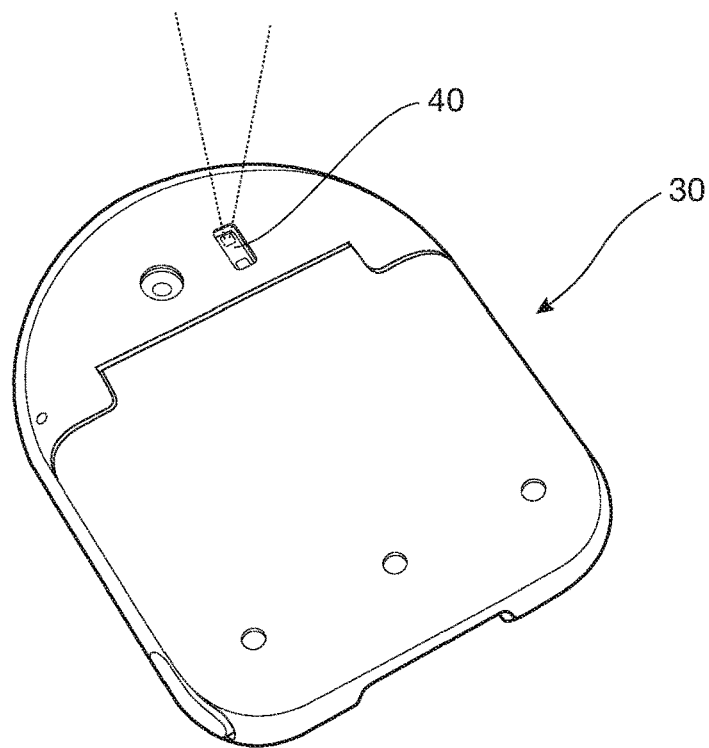
FIG. 2 illustrates a diagrammatic representation of the device of FIG. 1.
Figure 3:
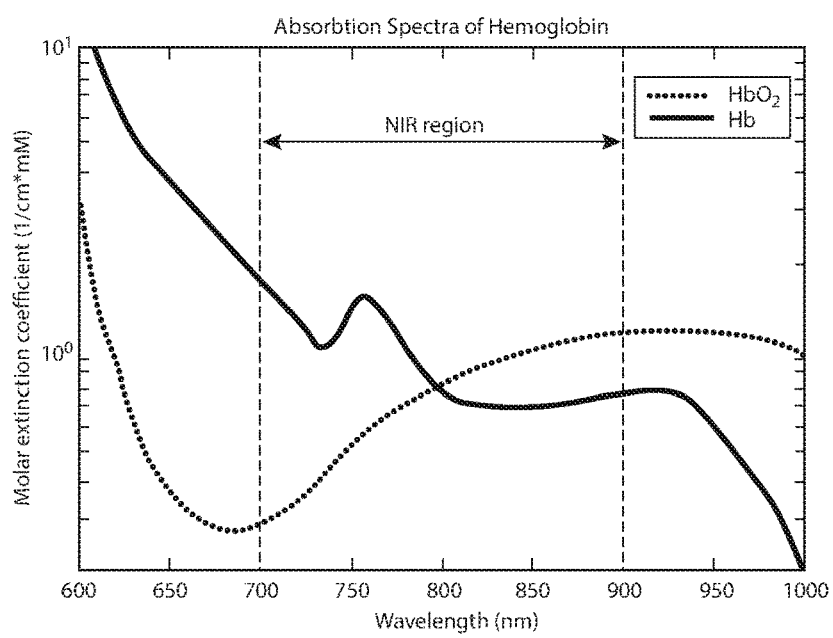
FIG. 3 illustrates an absorption spectrum diagram for oxygenated haemoglobin (HbO2) and deoxygenated haemoglobin (Hb) for red and infrared wavelengths.

As illustrated in FIG. 2, the device 30 includes an oxygen saturation sensor 40 for monitoring the oxygen saturation of the blood of the wearer. Oxygen saturation sensors exist and are referred to as pulse oximeters. Pulse oximetry measures arterial oxygen saturation based on the light absorption properties of blood. As illustrated in the graph in FIG. 3, when it combines with oxygen, deoxyhemoglobin (Hb) changes its light absorption characteristics. Pulse oximetry exploits the light absorption difference between Hb and oxygenated haemoglobin ($HbO_2$). Oxygen saturation $HbO_2$ absorbs more infrared light (660 nm wavelength) and lesser red light (940 nm wavelength) than Hb.

Figure 4:
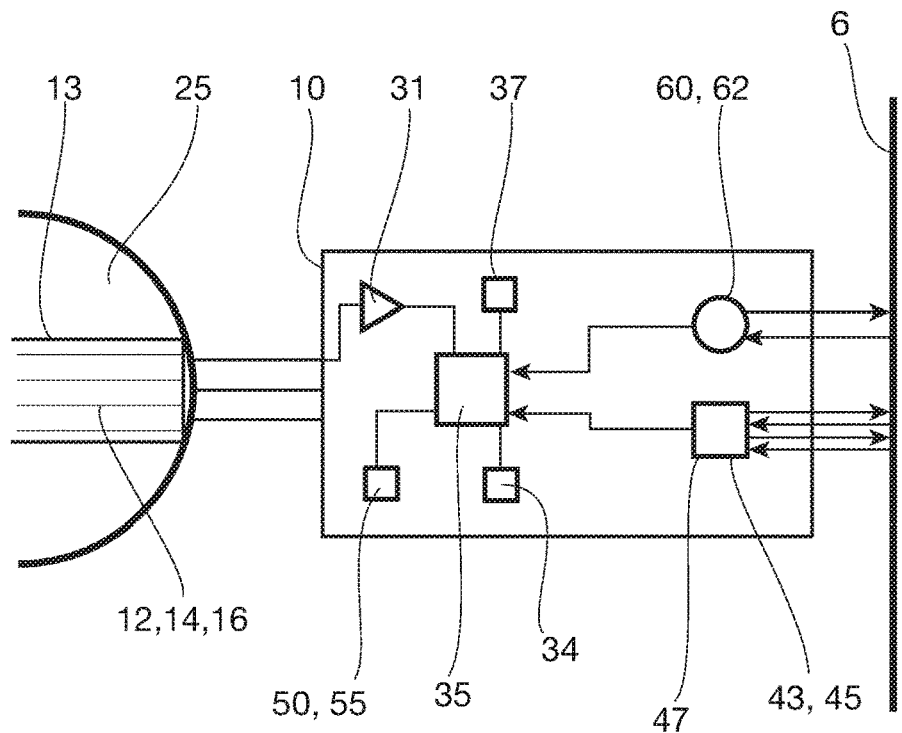
FIG. 4 illustrates a schematic diagram of the system of claim 1 including a plurality of electrodes on an absorbent article and a device for electrical connection with the electrodes and illustrating the operation of the pulse oximeter, accelerometer and temperature sensor.

FIG. 4 provides a schematic illustration of components of the device 30. The oxygen saturation sensor 40 comprises a pair of light emitting diodes (LEDs) 43, 45 and a photodetector 47 such as a photodiode. The LEDs 43, 45 and the photodetector 47 are electrically connected, such as via a circuit board, to other components onboard the device 30 including a processor 35 and a power supply, preferably in the form of a battery 37 which may be a rechargeable battery.

As will be described in further detail below, operation of the oxygen saturation sensor 40 requires locating the LEDs 43, 45 close to the wearer's skin. The device 30 is adapted to be mounted to an absorbent article 25 and electrically connected with the electrodes 12, 14, 16 so that when the absorbent article is worn by a wearer the device 30 is located in the groin or waist region. Accordingly, the device 30 is configured so that the LEDs 43, 45 and the photodetector 47 are located close to the wearer's skin 6 in the groin or waist region.

Figure 5:
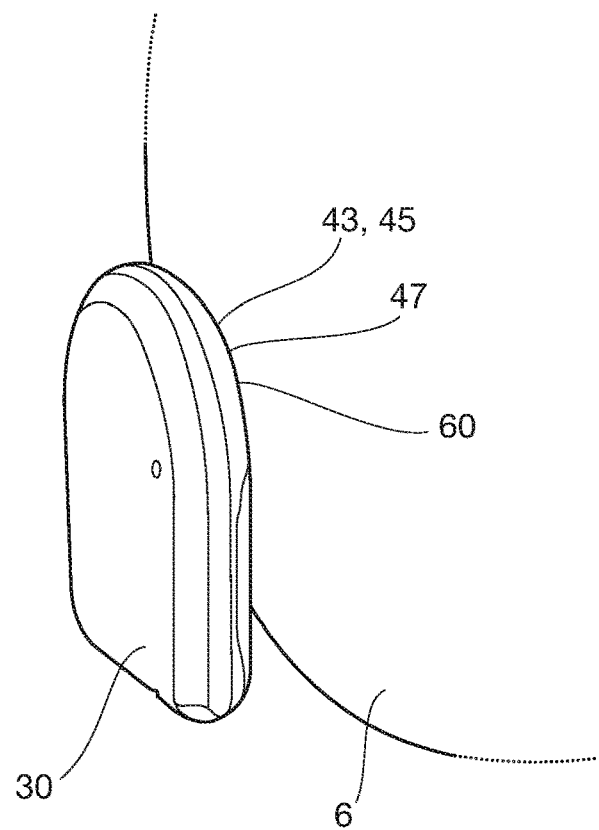
FIG. 5 illustrates a diagrammatic representation of the device of FIG. 1 in close proximity to the skin of a wearer.

The LEDs 43, 45 and the photodetector 47 are located adjacent to each other and facing the same direction, namely towards the skin of the wearer wearing the device 30 as illustrated in FIGS. 4 and 5. The LEDs 43, 45 emit two wavelengths of light (i.e. infrared light (660 nm wavelength) and lesser red light (940 nm wavelength)) that are incident on the wearer's skin. Light is reflected back from the wearer that is incident on the photodetector 47 which is electrically connected to the processor 30. The processor 30 receives from the photodetector 47 signals that are indicative of the wavelengths and/or intensity of light incident on the photodetector 47. The processor 30 is configured to process the signals on-board, or alternatively data is processed in another processor, to determine the changing absorbance of light emitted by the LEDs 43, 45 at each of the wavelengths to thereby determine the absorbances due to the pulsing arterial and/or venous blood in the body of the wearer.

Figure 15:
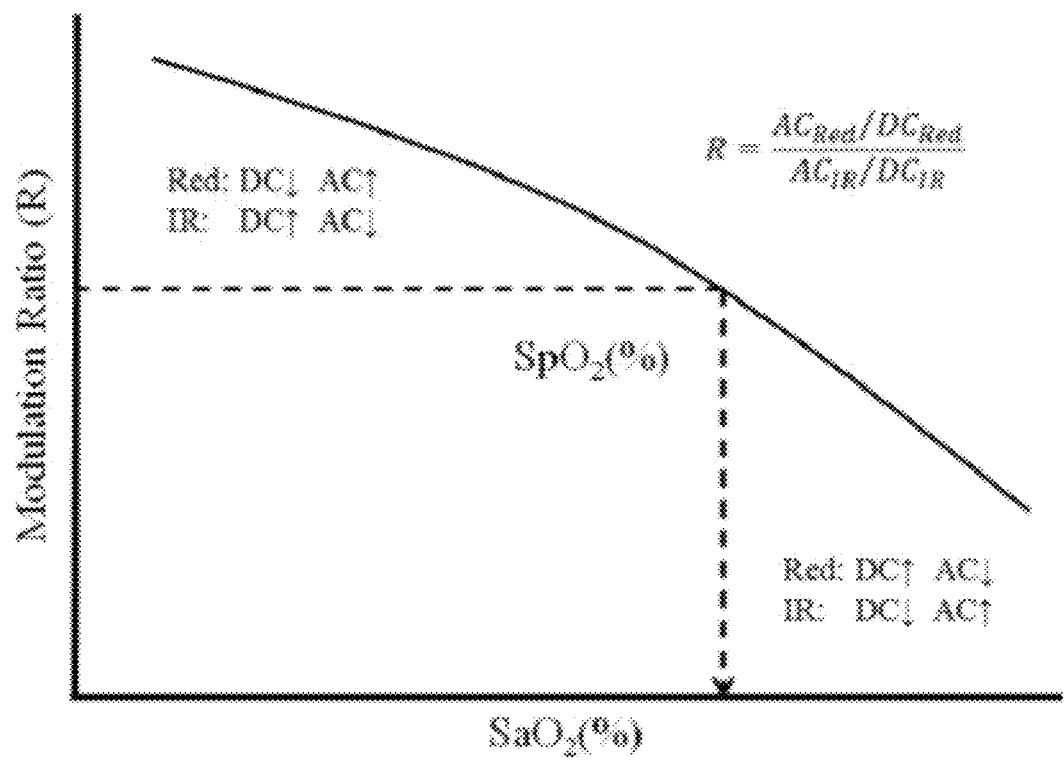
FIG. 15 illustrates a calibration curve which can be used to estimate $SaO_2$ based on the modulation ratio calculated by pulse oximetry using the DC and AC components of the red and infrared signals.

The reflected light signals consist of a direct current (DC) component and pulsatile alternating current (AC) component. Pulse oximetry calculates the modulation ratio R by using the DC and AC components of the red and infrared signals as follows:

$$R = \frac{AC_R/DC_R}{AC_{IR}/DC_{IR}},$$

where $AC_R$ and $AC_{IR}$ are the AC amplitudes of the red and infrared signals, respectively. Then, empirically derived calibration curves are used to estimate $SaO_2$ based on the modulation ratio R, as seen in FIG. 15.

Figure 16:
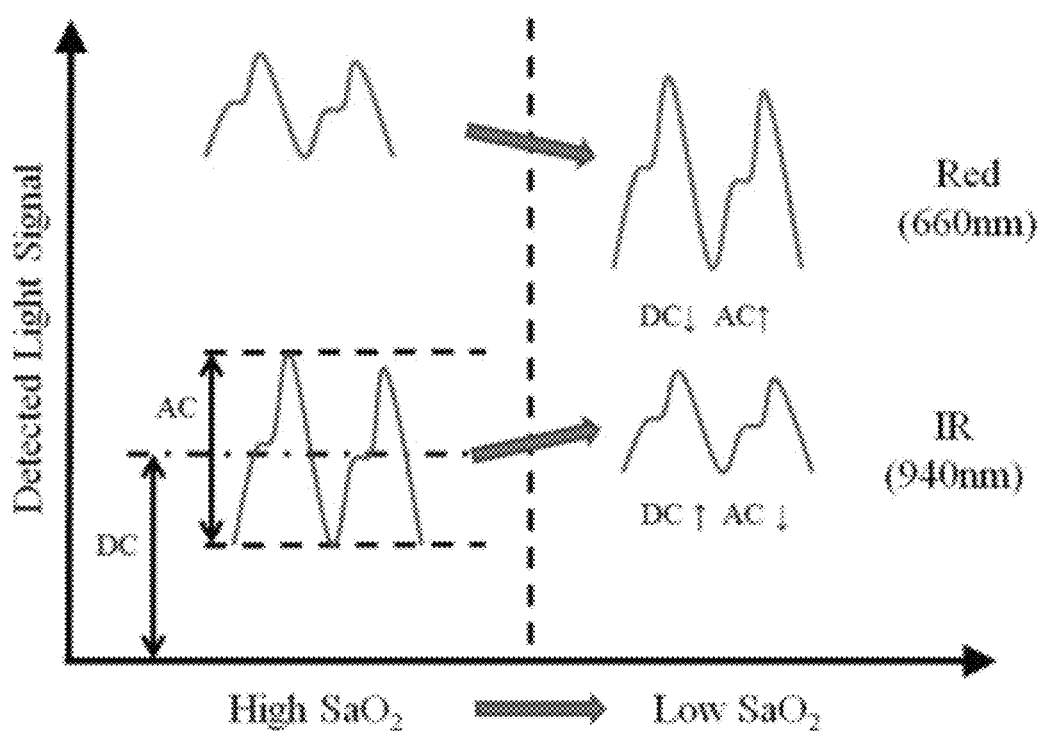
FIG. 16 illustrates light signals for red and infrared light at high and low $SaO_2$ levels.

$AC_R$ and $DC_{IR}$ increase with decreasing $SaO_2$, as FIG. 16. On the other hand, $AC_{IR}$ and $DC_R$ decrease.

Accordingly, the offsets between the reflected red and infrared light detected by the photodetector is used by the processor 30 to calculate the oxygen saturation ($SaO_2$) of the arterial and/or venous blood in the body of the wearer.

The device 30 is configured so that the operation of the oxygen saturation sensor 40 is controlled according to the body position of the wearer wearing the device 30. Controlling the operation of the oxygen saturation sensor 40 includes controlling an intensity of light emitted by the LEDs 43, 45. The intensity of light emitted by the LEDs is controlled by adjusting the intensity of light emitted by the LEDs to different intensity emission settings. The processor 35 is adapted to adjust the current provided to the LEDs 43, 45 to thereby provide for the different light intensity emission settings. As will be described below, the processor 35 is configured to adjust between the different light intensity settings according to data indicative of the body position, or posture, of the wearer of the device 30.

When a wearer wearing the device 30 is lying down, the oxygen saturation sensor 40 of the device 30 is in closer proximity to the skin of the wearer and/or is being pressed with greater force against the skin of the wearer. This is particularly the case where the device 30 is attached to an incontinence garment such as a diaper or pad such that the device 30 is located at the groin or the waist of the wearer. The extent to which the device 30 is pressed against the skin of the wearer is at least in part due to the influence of gravity as well as other forces applied by the absorbent article 25 or an elastic band for carrying the device 30.

When the oxygen saturation sensor 40 of the device 30 is in closer proximity to the skin of the wearer and/or is being pressed with greater force against the skin of the wearer the intensity of light emitted from the LEDs 43, 45 needed for the photodetector 47 to detect a sufficient intensity of reflected light from the wearer's body to provide a sufficiently accurate and reliable indication of oxygen saturation is lower.

When a wearer wearing the device 30 is standing, the oxygen saturation sensor 40 of the device 30 is located further away from the skin of the wearer and/or is being pressed with less force against the skin of the wearer compared with the aforementioned case of the wearer lying down. When the oxygen saturation sensor 40 of the device 30 located further away from the skin of the wearer and/or is being pressed with less force against the skin of the wearer the intensity of light emitted from the LEDs 43, 45 needed for the photodetector 47 to detect a sufficient intensity of reflected light from the wearer's body is higher. This can be because the intensity of light incident on the wearer's body is proportional to the distance between the LEDs 43, 45 and the wearer's body and/or the propensity of the wearer's skin to allow light to pass through is proportional to the force with which the oxygen saturation sensor 40 of the device 30 is pressed against the skin of the wearer. The intensity of light reflected back to the photodetector 47 is also proportional to the distance between the wearer's body and the photodetector and/or the propensity of the wearer's skin to allow light to pass through which is proportional to the force with which the oxygen saturation sensor 40 of the device 30 is pressed against the skin of the wearer. Accordingly, the sensitivity of the oxygen saturation sensor 40 is very sensitive to the distance between the sensor 40 and the body of the wearer.

When a wearer wearing the device 30 is seated, the oxygen saturation sensor 40 of the device 30 is likely to be located an intermediate distance away from the skin of the wearer and/or is being pressed with a force against the skin of the wearer that is greater than when the wearer is lying and less than when the wearer is standing. When the oxygen saturation sensor 40 of the device 30 is located an intermediate distance away from the skin of the wearer and/or is being pressed with an intermediate force against the skin of the wearer the intensity of light emitted from the LEDs 43, 45 needed for the photodetector 47 to detect a sufficient intensity of reflected light from the wearer's body is at an intermediate level.

Accordingly, the device 30 is configured to adjust the current provided to the LEDs 43, 45 to different levels to thereby adjust the emitted light intensity to levels sufficient for providing an accurate and reliable indication of oxygen saturation in different postures such as lying down, seated and standing. Accordingly, the device 30 is configured so that the processor 35 adjust the drive current provided to the LEDs 43, 45 between at least two or preferably at least three settings including a lying down or prone setting (i.e. lowest current); a seated setting (i.e. intermediate current); and a standing setting (i.e. highest current).

The device 30 further includes a body position sensor 50 for detecting the body position of the wearer. In the illustrated embodiment, the device 30 includes an accelerometer 55, which may be comprised of a mechanical accelerometer such as an electrical, piezoelectric, piezoresistive or capacitive accelerometer. Alternatively, a small micro-electromechanical systems (MEMS) accelerometer may be employed.

The body position sensor 50 is electrically connected, such as via a circuit board, to other components onboard the device 30 including the processor 35. The processor 35 is configured to receive input from the body position sensor 50 to determine the posture of the wearer of the device 30, such as whether the wearer is lying down (i.e. prone), seated or standing. In a preferred form, the processor 35 processes signals from the accelerometer 55 to determine data indicative of the body position of the wearer. The processor 35 is also configured to adjust the drive current provided to the LEDs 43, 45 and thereby adjust the intensity of the light emitted therefrom based on the posture of the wearer.

In another embodiment, the processor 35 is adapted so that a sensitivity to the signals received from the photodetector 47 is adjusted according to the posture of the wearer in addition to or instead of adjusting the drive current provided to the LEDs 43, 45. Adjusting the sensitivity of the photodetector 47 can also provide for an accurate and reliable indication of oxygen saturation in different postures such as lying down, seated and standing.

Embodiments of the device 30 that are configured to determine the body position of the wearer and to adjust the operation of the oxygen saturation sensor 40 are advantageous in that they provide a sufficiently accurate and reliable indication of oxygen saturation in the blood of the wearer with minimal power consumption necessary to drive the LEDs 43, 45.

Accordingly, the processor 35 receives from the photodetector 47 signals that are indicative of the wavelengths and/or intensity of light incident on the photodetector 47. The processor 35 process the signals on-board, or alternatively data is processed in another processor, to determine the oxygen saturation (SaO2) of the arterial and/or venous blood in the body of the wearer. In embodiments, the processor 35 is also configured to receive an input from the body position sensor 50 to determine the posture of the wearer of the device 30, such as whether the wearer is lying down, seated or standing. In embodiments, the processor 35 is also configured to adjust the current provided to the LEDs 43, 45 to different levels to thereby adjust the emitted light intensity to levels according to the posture of the wearer as determined by the processor 35 to provide an accurate and reliable indication of oxygen saturation in different postures such as lying down, seated and standing.

Figure 7:
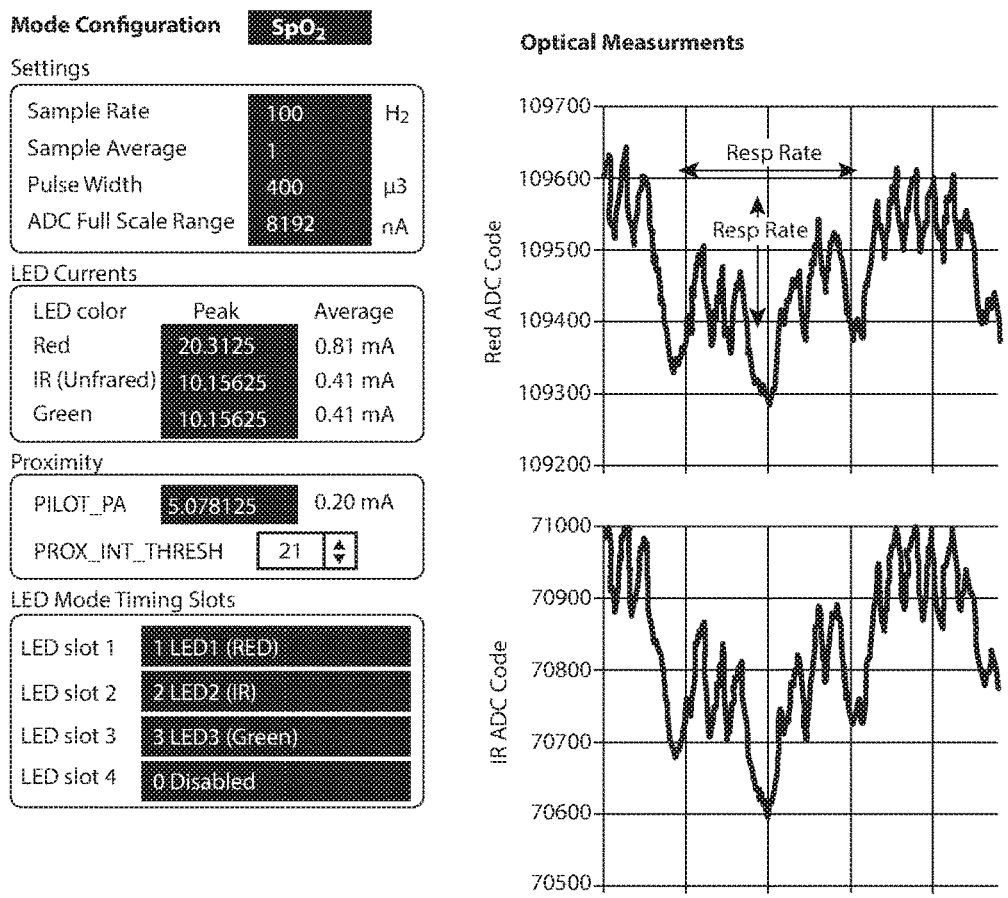
FIG. 7 are graphs plotting data received from the photodetector of the pulse oximeter of the device of FIG. 1.

In embodiments, the signals received from the photodetector 47 indicative of the light reflected from the body of the wearer is processed by the processor 35 to determine other physiological parameters. As illustrated in FIG. 7, the heart rate, respiration rate and respiration depth of the wearer is also determined from the signals received from the oxygen saturation sensor.

Figure 6:
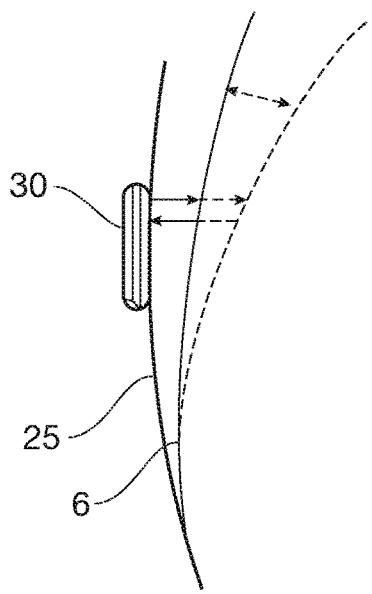
FIG. 6 illustrates a schematic diagram of the system of FIG. 1 in close proximity to the skin in the groin or waist region of the wearer.

Referring to FIG. 6, it has been found that the location of the device 30, including the oxygen saturation sensor 40 in the vicinity of the groin or the waist of the wearer, produces signals relating to heart rate, respiration rate and respiration depth. The location of the device 30 in the groin or waist region of the wearer means that movement of the wearer's groin or waste caused by movement of the diaphragm during inhalation and exhalation is revealed in the signals from the oxygen saturation sensor 40. Accordingly, in the signal received by the processor 35 from the oxygen saturation sensor 40 is data indicative of respiration rate and/or depth of the wearer.

In FIG. 7, the heart rate of the wearer is indicated by the local maxima and minima in the signal. The respiration rate is indicated by the period between global maxima or global minima in the signal. The respiration depth is indicated by the difference in magnitude of the signal between the median or average of the signal over successive oscillations comprising local maxima and minima in relatively close proximity to each other.

FIG. 7 illustrates a time domain signal comprising three distinct sequences of oscillations in which the local maxima are relatively close to each other, or within a given tolerance, and local minima are relatively close to each other, or within a given tolerance.

In particular in the Red spectrum, a first sequence in which the local maxima and minima are in a range between about 109500 and 109700, a second sequence in which the local maxima and minima are in a range between about 109300 and 109500 and a third sequence in which the local maxima and minima are in a range between about 109500 and 109700. In the Infra-Red spectrum a first sequence in which the local maxima and minima are in a range between about 70900 and 71000, a second sequence in which the local maxima and minima are in a range between about 70600 and 70900 and a third sequence in which the local maxima and minima are in a range between about 70900 and 71000.

Embodiments of the invention involve analysing the signals in the frequency domain, for example by conducting a spectral analysis. For example, to identify prominent or dominant frequencies that may be indicative of, or may distinguish between, heart rate and respiration rate. In an embodiment, the processor 35 is configured is configured to execute a Fourier transform to convert the signal's time-domain representation, shown in FIG. 7, to the signal's frequency-domain representation. The component frequencies, spread across the frequency spectrum, are represented as peaks in the frequency domain. The component frequencies, as determined by spectral analysis, can be indicative of heart rate and respiration rate of the wearer.

The respiration rate is determined by reference to a measurement of a time period between the three sequences. Such a measurement may include a period between a beginning, midpoint or endpoint of the first sequence and a beginning, midpoint or endpoint of the second sequence or a beginning, midpoint or endpoint of the second sequence to a beginning, midpoint or endpoint of the third sequence.

The respiration depth is determined by reference to a measurement of a difference between the signals in the time interval associated with the three sequences. Such a measurement includes a difference between the median or the average signal over the time interval associated with each sequence.

The location of the device 30 in the groin or waist region of the wearer means that movement detected by the accelerometer is indicative of movement of the wearer's groin or waste caused by movement of the diaphragm during inhalation and exhalation. Accordingly, in the signal received by the processor 35 from the accelerometer 55 is data indicative of respiration rate and/or depth of the wearer. In particular, the signal received by the processor 35 from the accelerometer 55 includes data indicative of movement of the wearer's groin or waste caused by movement of the diaphragm during inhalation and exhalation. Processing of the signal from the accelerometer 55 by the processor 35 provides data indicative of respiration rate and respiration depth of the wearer. In an embodiment, the respiration rate and respiration depth data determined from the signal from the accelerometer 55 is compared with the respiration rate and respiration depth data obtained from processing the signal from the oxygen saturation sensor 40 to verify the data.

The device 30 also includes a contactless temperature sensor 60 for detecting the temperature of the skin of the wearer. The temperature sensor 60 includes an infra-red pyrometer electrically connected, such as via a circuit board, to other components onboard the device 30 including the processor 35 and the battery 37. The processor 35 processes signals from the pyrometer to determine data indicative of the body temperature of the wearer.

The temperature sensor 60 includes an infra-red pyrometer 62 and the processor 35 is configured for processing signals from the pyrometer 62 to determine data indicative of the body temperature of the wearer.

The plurality of electrodes 12, 14, 16 on the absorbent article 25 are comprised of at least two and preferably three mutually separated, flexible, conductive printed electrodes. In particular, the electrodes 12, 14, 16 are carbon strips which are printed on a substrate which is the applied to the absorbent article or is incorporated in the process of manufacturing absorbent article 25.

The device 30 includes a set of electrical contacts (not shown) adapted for connection with the electrodes 12, 14, 16. The contacts may be in the form of prongs adapted to be forced through respective ones of the electrodes 12, 14, 16 and form an electrical connection therewith. The electrodes 12, 14, 16, or at least a portion of the electrodes 12, 14, 16 for establishing an electrical contact with the contacts of the device 30, are each located in a respective transverse location without any overlap such that each one of the prong-shaped electrical contacts will penetrate and establish an electrical contact with only a respective one of the electrodes 12, 14, 16. Alternatively, the device 30 may be configured for contactless connection with the electrodes 12, 14, 16.

The device 30 is adapted for monitoring one or more electrical properties of the electrodes 12, 14, 16 such as the resistance, voltage or capacitance between the electrodes 12, 14, 16. A signal conditioner 31 is included in the circuit between the electrodes 12, 14, 16 and the processor 35. Upon the ingress of water or some other fluid or urine or faecal constituent into the absorbent layer 27, such as with the occurrence of a urinary or faecal incontinence event, changes in the electrical properties of the electrodes 12, 14, 16 may be detected by the device 30 as described in the foregoing.

In the illustrated embodiment, the electrodes 12, 14, 16 are provided on the water impermeable outer layer 29 and/or on a water impermeable substrate 13 which may then be applied to the outer layer 29 (either permeable or impermeable). An insulating layer 15 may be applied to the electrodes 12, 14, 16. The electrodes thereby form a non-polar variable electrolytic capacitor. Pairs of the electrodes 12, 14, 16 serve as two electrodes of the electrolytic capacitor. The insulation 15 and/or the water impermeable outer layer 29 and/or the substrate 13 serve as a dielectric of the electrolytic capacitor. The liquid or other urine or faecal constituents in the absorbent layer 27 serves as an electrolyte (electrolyte solution) of the electrolytic capacitor. The capacitance value of the electrolytic capacitor is related to the content and distribution of the liquid or other urine or faecal constituents contained in the absorbent layer 27. The wetness state, or soiled state, of the absorbent layer 27 of the absorbent article 25 can be obtained by detecting the capacitance value, or voltage, of the electrolytic capacitor and analyzing the pattern of changes in the capacitance value.

Accordingly, the electrical property exhibited by the electrodes 12, 14, 16 that principally changes following the ingress of water or other urine or faecal constituents into the absorbent layer 27 is capacitance or voltage. Over time, as more incontinence events occur, more water or other urine or faecal constituents is absorbed into the absorbent layer 27 and this is detected in a further change in capacitance value or voltage. The capacitance value is useful in indicating qualitative information such as the presence of liquid associated with a urinary incontinence event and also quantitative information such as the volume of liquid in a urinary incontinence event or the cumulative amount of liquid present in the absorbent layer or core 27.

As described above, embodiments of the device 30 include the processor 35, the battery 37, the oxygen saturation sensor 40, the accelerometer 55 and the temperature sensor 60. Embodiments of the device 30 also include an on-board memory and a transmitter/receiver 34. The memory has a relatively small capacity in order to keep the cost of the device 30 as low as possible. As such the device 30 has a limited capacity to store data generated by the processor that is indicative of the electrical properties of the electrodes 12, 14, 16 that are monitored by the device 30. Furthermore, because the memory and the power supply on the device 30 have relatively small capacities, the device 30 is configured to transmit data wirelessly and in small data packets over short distances, preferably to a receiving device 110 such as a smartphone device or a tablet or a fixed device (e.g. Room Monitor) or a smartwatch, that are near or come near the device 30. Preferably, the transmitter/receiver 34 is configured to transmit and receive data wirelessly using the Bluetooth standard. The receiving device 110 are remotely located from the transmitting device 30 and is preferably also configured to receive data via the Bluetooth standard. The system 1 may be configured to require or not require pairing of the transmitting device 34 and the receiving device 110.

Since the memory of the transmitting device 30 is limited, or the transmission packet size is limited, the device 30 cannot store all of the data that it collects. The device 30 is configured to process the data indicative of the electrical behaviour of the electrodes 12, 14, 16 and determine what information is relevant to determine the status of the absorbent article 25, for example the occurrence of a urinary and/or faecal incontinence event, cumulative volume of wetness present in the absorbent article from multiple incontinence events, the times when incontinence events occur, or the volume of each individual incontinence event. Alternatively, the device 30 may carry out no or minimal pre-processing and may send raw time-based data to any one or more receiving devices 110 for storage and further processing.

The device 30 is deliberately designed for low power consumption. To this end, the device employs a memory of relatively limited capacity, the processor 35 has relatively limited computational power, the device 30 is configured for relatively low frequency data sampling or sensing (i.e. in the order seconds rather than small fractions of a second). The device 30 is preferably configured for relatively low frequency data sampling, such as every few seconds or even minutes, in relation to the electrodes 12, 14, 16 (i.e. when monitoring resistance and/or capacitance). Low power consumption of the device 30 is further enhanced by providing for adjustment of the current provided to the LEDs 43, 45 to different levels according to the posture of the wearer.

Accordingly, this disclosure provides a reliable and cost effective system 1 for full-time monitoring of incontinence events in an absorbent article worn by a wearer and for full-time monitoring of physiological parameters that may be indicative of changing health conditions such as respiratory distress or fever is possible.

In embodiments, the system 1, including the combination of the wearable device 30, the absorbent article 25 and the electrodes 12, 14, 16, is capable of full-time monitoring any one or more of: the oxygen saturation (SaO2) of the arterial and/or venous blood in the body of the wearer; the posture of the wearer; incontinence status of the absorbent article 25; the body temperature of the wearer; heart rate; respiration rate; and respiration depth.

In embodiments, the system 1 is configured so that the processor 35 in the device 30 can determine the posture of the wearer and adjust the operation of the oxygen saturation sensor 40 according to the determined posture so that the minimal necessary power is consumed to drive the LEDs 43, 45 that provides a sufficiently accurate and reliable indication of oxygen saturation in the blood of the wearer.

In embodiments, the signals received from the photodetector 47 of the oxygen saturation sensor 40 indicative of the reflected light is processed by the processor 35 to determine other physiological parameters. In particular, as illustrated in FIG. 7, the heart rate, respiration rate and respiration depth of the wearer is determined from the signals received from the oxygen saturation sensor 40.

Wherever it is mentioned in this specification that processing is conducted, such as by the processor 35 or otherwise, such processing may be conducted in the processor 35, or in a processor located remotely in a device or a server or in a cloud computing processor or may be distributed amongst any combination thereof.

The data collected by the system 10 can be used for full-time monitoring of incontinence events in an absorbent article worn by a wearer and for full-time monitoring of physiological parameters that may be indicative of changing health conditions such as respiratory distress or fever. If the system 10 determines if an incontinence event has occurred in an absorbent article, or some other physiological parameter being monitored indicative of changing health conditions (e.g. respiratory distress or fever), the receiving device 110 may be configured to display an alert. Alternatively, the system 10 enables a user to set thresholds or targets for parameters such as: the oxygen saturation (SaO2) of the arterial and/or venous blood in the body of the wearer; the posture of the wearer; incontinence status of the absorbent article 25; the body temperature of the wearer; heart rate; respiration rate; and respiration depth. The system 10 may be further configured for the device 110 to display if any one of more of the thresholds or targets has been exceeded. In embodiments, the thresholds or targets are user configurable.

Figure 8:
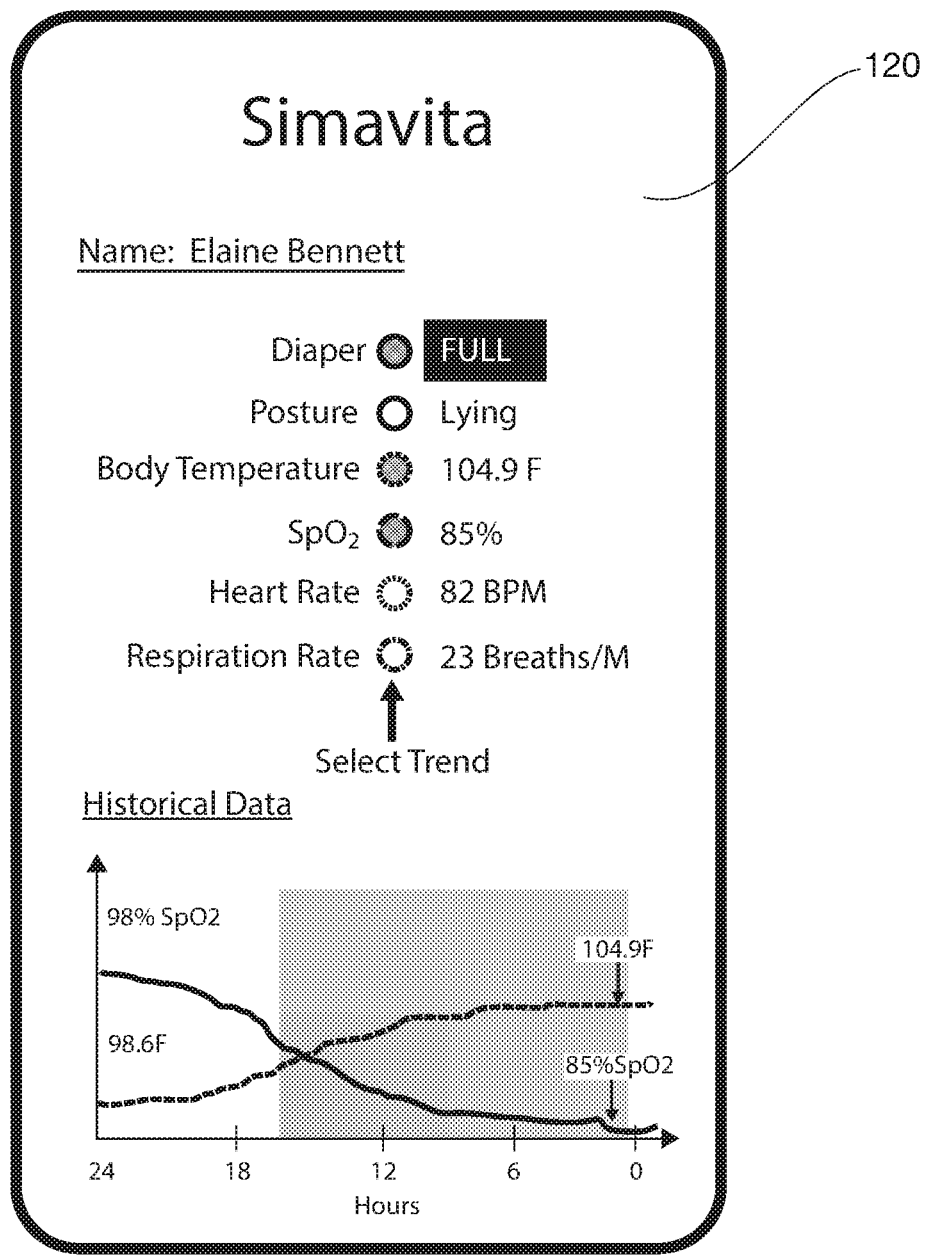
FIG. 8 illustrates a graphical interface of a device for presenting information to a user in accordance with an embodiment of the system of FIG. 1 including data representative of oxygen saturation, posture, incontinence status, body temperature, heart rate, respiration rate and respiration depth.

The system 10 is preferably configured so that data representative of oxygen saturation, posture, incontinence status, body temperature, heart rate, respiration rate and respiration depth is presented graphically on a device screen 120 or a user interface as shown in FIG. 8. As illustrated in FIG. 8, the system 10 may also be configured to present representations of historical data such as oxygen saturation and body temperature.

Figure 9:
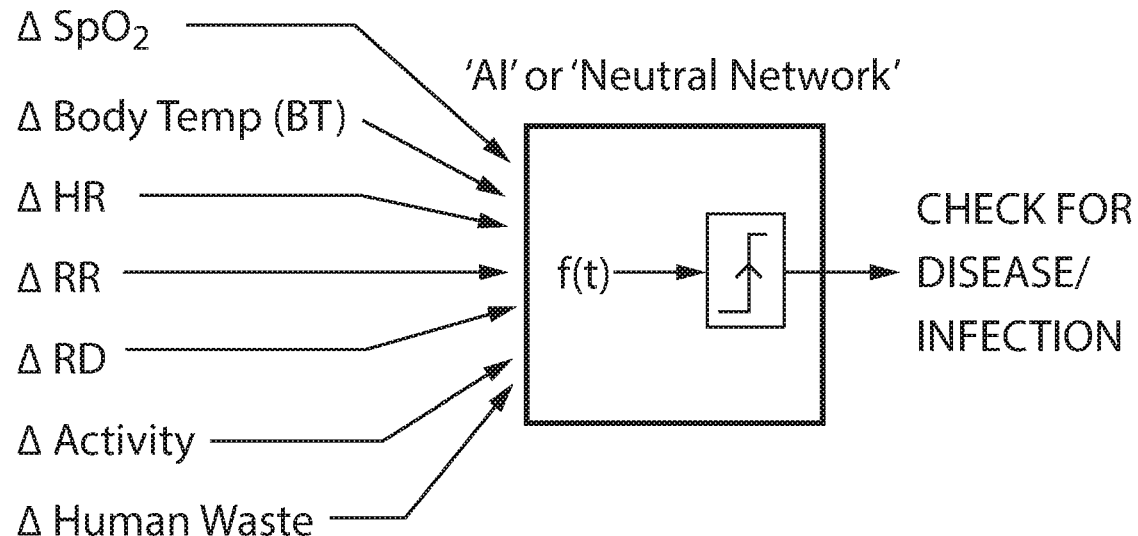
FIG. 9 illustrates an algorithm to provide an alert of the possibility that a health condition or disease may be present in a wearer of the device of FIG. 1.
Figure 9:
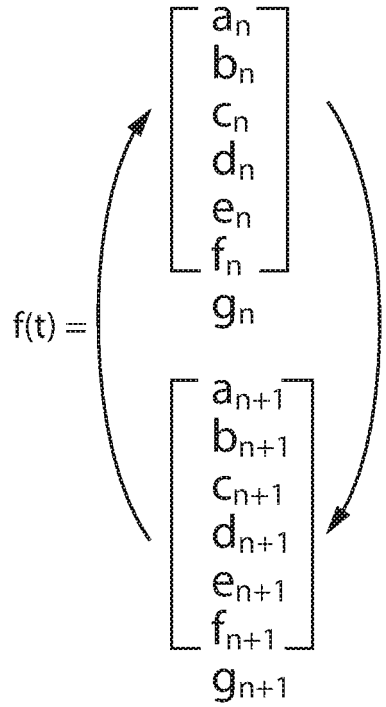

FIG. 9 illustrates an algorithm to provide an alert of the possibility that a health condition or disease may be present in the wearer. The algorithm contains constants a to g which can be updated using a learning algorithm such as neural network or AI. In particular, the algorithm is adapted to process information relating to variables such as: change in oxygen saturation, change in body temperature, change in heart rate, change in respiration rate; change in respiration depth, change in activity, change in incontinence. The information is processed via an artificial intelligence algorithm such as a neural network to generate an output such as determining if the wearer is likely suffering from a disease or infection and that manual investigation and diagnosis is warranted.

In one embodiment, the algorithm may involve applying a function including: allocating a weighting to each one of the variables; calculating a sum of the weighted variables; and determining if the sum of the weighted variables exceeds a threshold in which case a disease or infection is indicated. In an embodiment, a user such as a clinician can train or otherwise determine these variables and put boundaries on alerts or can program the system to ignore certain conditions. The algorithm may further include determining the weightings in an iterative process such as by applying an optimisation function. The optimisation function includes a neural network or a linear regression or a logistic regression or gradient descent.

Figure 10:
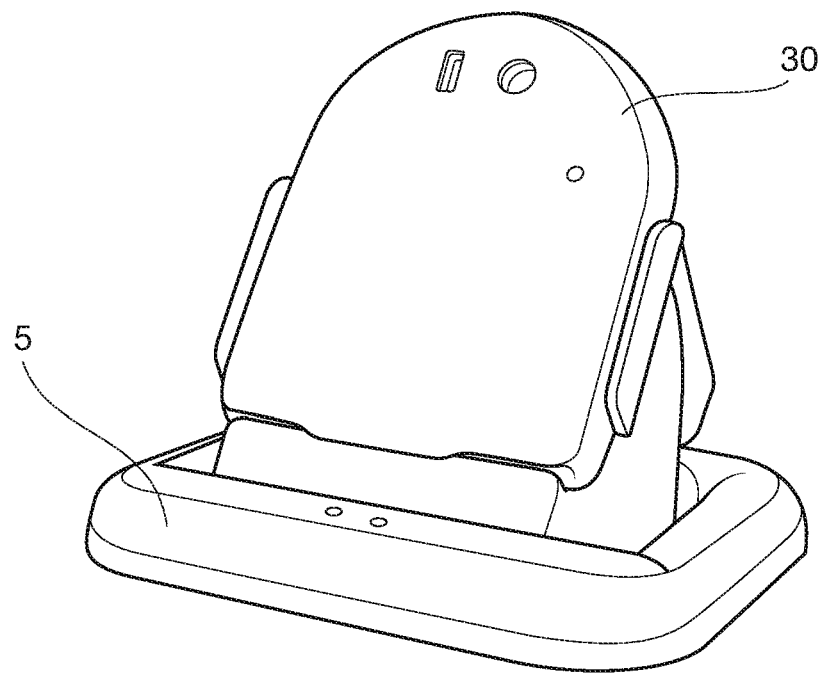
FIG. 10 illustrates a diagrammatic representation of an embodiment of the system of FIG. 1 including the device and a charging cradle wherein the device and cradle are configured for charging a battery in the device through a transfer energy therebetween via an inductive coupling.
Figure 11:
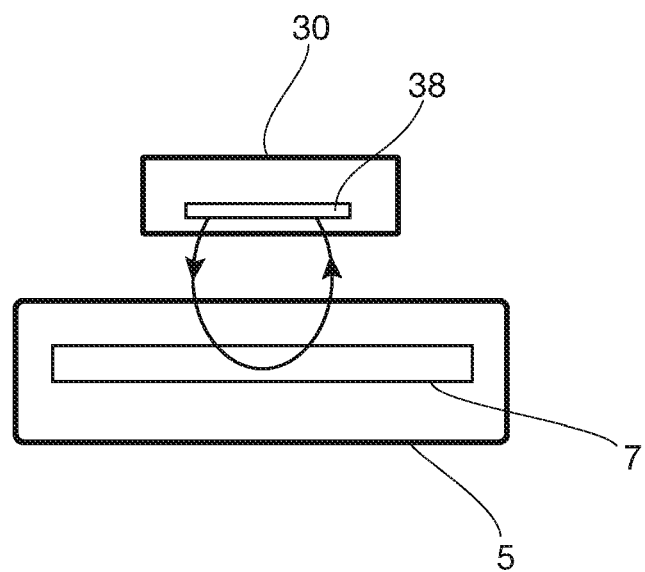
FIG. 11 illustrates a schematic representation of the device and charging cradle of FIG. 10.

Referring to FIGS. 10 and 11, an embodiment of the system 1 includes a form of the device 30 configured for wireless charging. A charging station 5 is provided that is adapted to receive the device 30 wherein the station 5 and the device 30 together are configured to transfer energy therebetween via an inductive coupling. The charging station 5 includes a primary coil 7 and a cradle to receive the device 30 as shown in FIG. 10. The device 30 includes a secondary coil 38 electrically connected to the battery 37. The charging station 5 and the device 30 facilitate convenient recharging of the battery 37 on board of the device 30.

In further embodiments, the invention relates to a system 101 for use within individuals who are not incontinent and that is for monitoring physiological parameters only and not for monitoring incontinence. In these embodiments the system 101 includes a version of the device 30 without electrical contacts, for electrical connection with the electrodes 12, 14, 16. Accordingly, the device 30 includes any one or more of the processor 35, the battery 37, the oxygen saturation sensor 40, the accelerometer 55 and the temperature sensor 60. The device 30 also includes a secondary coil 38 electrically connected to the battery 37 for charging via an inductance coupling.

The device 30 is preferably configured so that the processor 35 adjusts the drive current provided to the LEDs 43, 45 between at least two or preferably at least three settings including a lying down or prone setting (i.e. lowest current); a seated setting (i.e. intermediate current); and a standing setting (i.e. highest current).

The processor 35 is preferably also adapted to determine respiration rate and/or depth of the wearer from the from the oxygen saturation sensor 40 data and/or from the accelerometer 55 data. Alternatively, the system 101 enables a user to set thresholds or targets for parameters such as: the oxygen saturation (SaO2) of the arterial and/or venous blood in the body of the wearer; the posture of the wearer; the body temperature of the wearer; heart rate; respiration rate; and respiration depth. The system 101 may be further configured for the device 110 to display if any one of more of the thresholds or targets has been exceeded.

Figure 12:
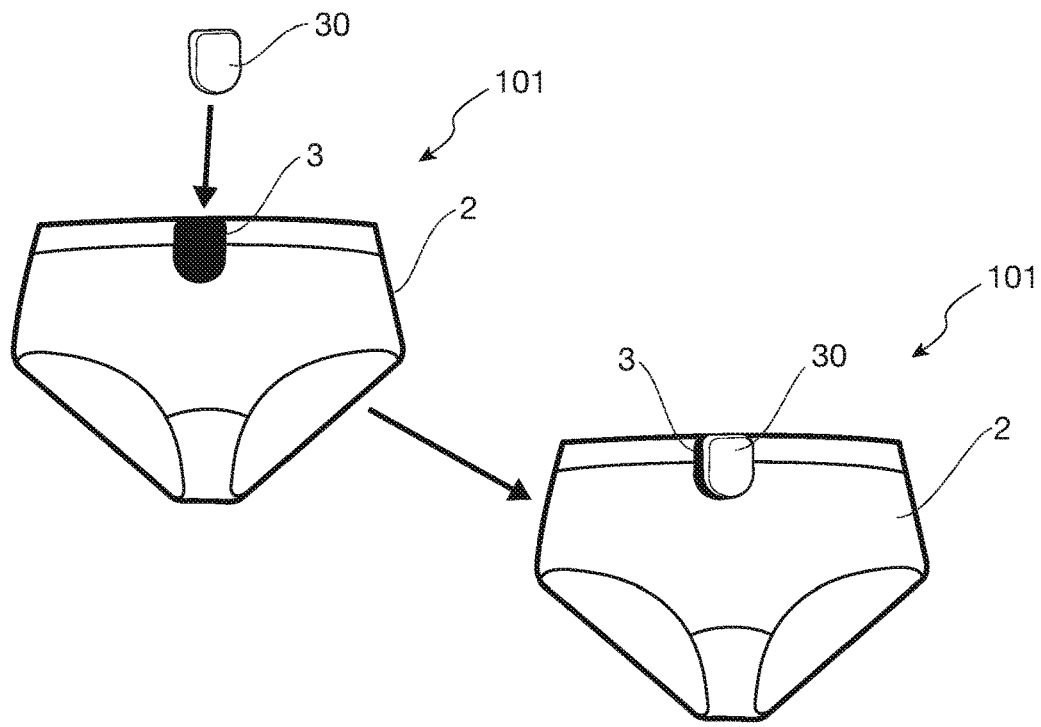
FIG. 12 illustrates an embodiment of the device for use within individuals who are not incontinent and that is for monitoring physiological parameters only and not for monitoring incontinence wherein the device can be fastened near and over the waist or groin area with either underwear or pants including an integrated pocket for the device.
Figure 13:
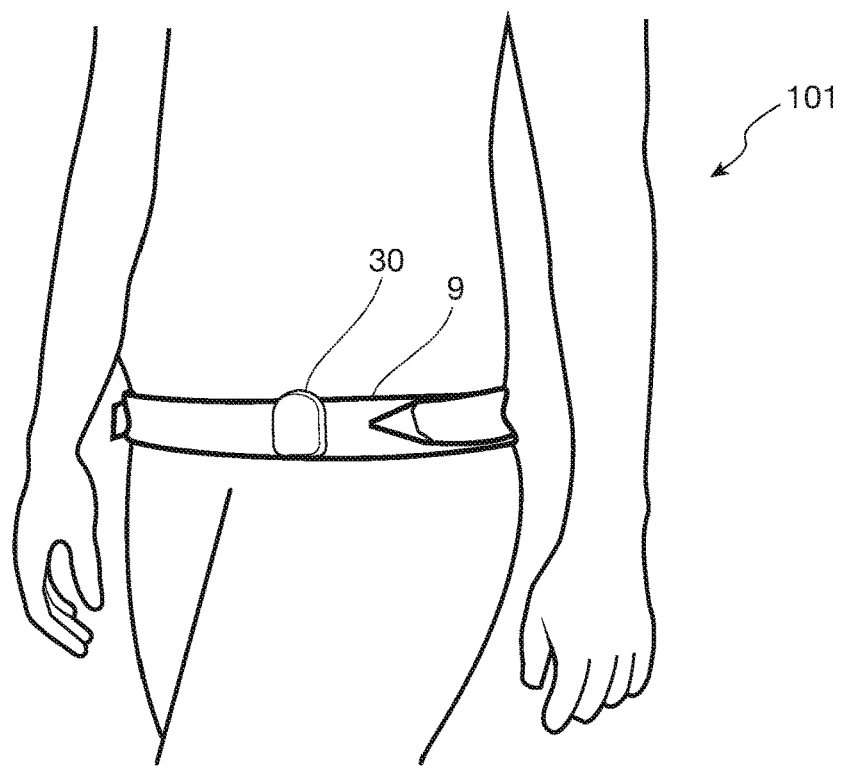
FIG. 13 illustrates the device of FIG. 12 fastened near and over the waist or groin area with a belt.

As shown in FIG. 12 the device 30 can be fastened near and over the waist or groin area with either underwear or pants 2 including an integrated pocket 3 for the device 30. As shown in FIG. 13, the device 30 can be fastened near and over the waist or groin area with a belt 9.

In an embodiment, the device 30 includes a microphone or an acoustic sensor, such as a MEMS microphone sensor. The sensor may be configured to "listen" to the lower bowel of the wearer, since the device 30 will be located in use in close proximity to the waist or groin region, for the purpose of detecting as a faecal voiding event as a bowel movement. The body position data determined in accordance with other embodiments described herein is preferably used to adjust or filter the data from the microphone for analysis.

Figure 14:
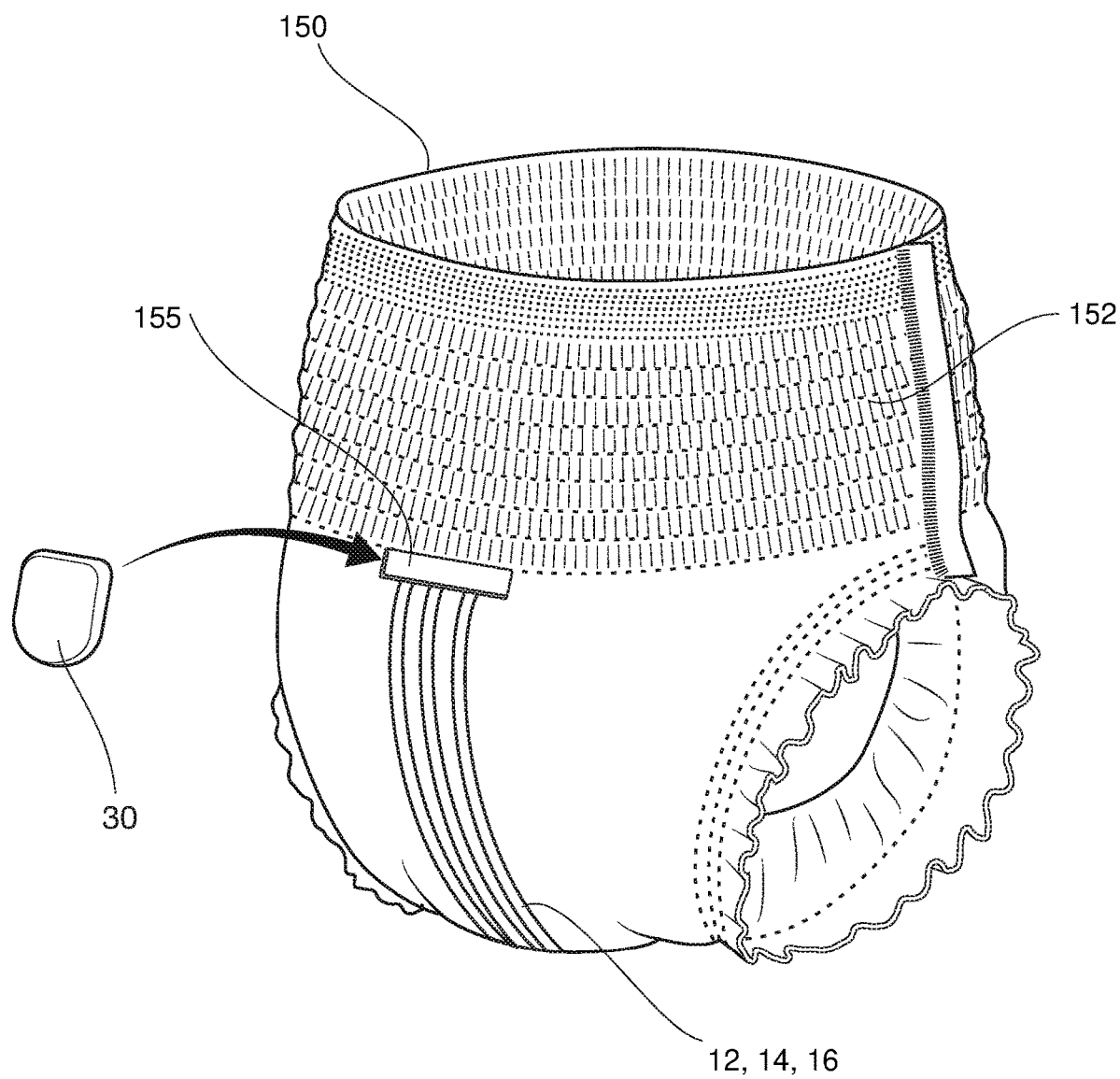
FIG. 14 illustrates an embodiment comprising a pants-type pull-up diaper including a plurality of electrodes and the device for electrical connection with the electrodes and an opening in the exterior shell of the diaper to enable insertion of the device therethrough.

FIG. 14 illustrates an embodiment comprising an absorbent article 25 comprised of a pants-type pull-up diaper 150 including the electrodes 12, 14, 16 provided on the water impermeable outer layer. The diaper 150 includes an opening 155 in the outer layer or exterior shell of the diaper 150 immediately below the gusseted waist elastic region 152. The device 30 is coupled to the electrodes 12, 14, 16 and is inserted through the opening 155 in the outer layer or exterior shell of the diaper 150 to enable the oxygen saturation sensor 40 and the temperature sensor 60 to be in contact with the wearer's skin. The device 30 preferably includes a provision to clamp or otherwise frictionally grip the electrodes 12, 14, 16 to establish an electrical connection with the set of electrical contacts of the device 30. Upon connection of the device 30 with the electrodes 12, 14, 16 the device 30 may be rotated in a sagittal plane and inserted through the opening 155.

The invention may be susceptible to other modifications or mechanical equivalents without departing from the spirit or ambit of the invention disclosed herein.

The invention claimed is:

1. A system for monitoring incontinence and physiological parameters, the system including:
   a plurality of electrodes on an absorbent article including an absorbent core to be worn by a wearer being monitored;
   a device for electrical connection with the electrodes and for monitoring one or more electrical properties of the electrodes indicative of the occurrence of an incontinence event;
   an oxygen saturation sensor for monitoring the oxygen saturation of the blood of the wearer;
   wherein the operation of the oxygen saturation sensor is controlled according to the body position of the wearer.

2. The system of claim 1, wherein the oxygen saturation sensor comprises a pair of light emitting diodes (LEDs) and a photodetector and a processor for determining oxygen saturation in the blood of the wearer, wherein controlling the operation of the oxygen saturation sensor includes controlling an intensity of light emitted by the LEDs.

3. The system of claim 2, wherein controlling an intensity of light emitted by the LEDs includes adjusting the intensity of light emitted by the LEDs between different intensity settings.

4. The system of claim 2, wherein a processor is adapted to adjust the current provided to the LEDs according to data indicative of the body position of the wearer.

5. The system of claim 4, wherein the processor is adapted to adjust a sensitivity to signals received from the photodetector in addition to or instead of adjusting the current provided to the LEDs.

6. The system of claim 2, wherein the processor determines the heart rate of the wearer from the signals received from the oxygen saturation sensor.

7. The system of claim 2, wherein the processor determines the respiration rate and/or the respiration depth of the wearer from the signals received from the oxygen saturation sensor.

8. The system of claim 2, wherein the processor includes any one or more of a processor in the device, a processor located in a device or a server located remotely of the device or a cloud computing processor or distributed among any combination thereof.

9. The system of claim 1, wherein the body positions include any one or more of a prone position, a seated position and a standing position.

10. The system of claim 1, wherein the device further includes a body position sensor for detecting the body position of the wearer.

11. The system of claim 10, wherein the body position sensor includes an accelerometer and a processor for processing signals from the accelerometer to determine data indicative of the body position of the wearer.

12. The system of claim 11, wherein data from the accelerometer is processed to determine movement of the wearer indicative of respiration rate and/or depth of the wearer.

13. The system of claim 1, wherein the device further includes a contactless temperature sensor for detecting the temperature of the skin of the wearer.

14. The system of claim 13, wherein the contactless temperature sensor includes an infra-red pyrometer and a processor for processing signals from the pyrometer to determine data indicative of the body temperature of the wearer.

15. The system of claim 1, wherein the electrodes are comprised of at least two mutually separated flexible conductive electrodes wherein an electrical property of the electrodes being monitored is capacitance.

16. The system of claim 15, wherein the electrodes are disposed on an outer surface of a water impermeable layer of the absorbent article facing away from the wearer with the absorbent core located on an opposite side of the water impermeable layer facing towards the wearer.

17. The system of claim 15, including a processor for monitoring the capacitance of the electrodes to determine data indicative of the occurrence of an incontinence event in the absorbent article.

18. A method for monitoring incontinence and physiological parameters, the method including:
   electrically connecting a device to electrodes applied to an absorbent article worn by a wearer;
   monitoring an electrical property exhibited by the electrodes;
   detecting a change in the electrical property due to the presence of fluid from a urinary incontinence event or constituents of a faecal incontinence event in the absorbent article;
   determining from the change in the electrical property the occurrence of a urinary or faecal incontinence event;
   receiving and processing data from an oxygen saturation sensor for monitoring oxygen saturation in the blood of the wearer;
   receiving and processing data from a body position sensor for determining the body position of the wearer; and
   controlling the operation of the oxygen saturation sensor according to the determined body position of the wearer.

19. The method of claim 18, wherein controlling the operation of the oxygen saturation sensor includes controlling an intensity of light emitted by a pair of light emitting diodes (LEDs) and/or adjusting a sensitivity to signals received from a photodetector.

20. The method of claim 18, including determining the respiration rate and/or the respiration depth of the wearer from the signals received from the oxygen saturation sensor.

* * * * *